(12) United States Patent
Mohammadi et al.

(10) Patent No.: US 7,588,775 B2
(45) Date of Patent: Sep. 15, 2009

(54) SILICONE ELASTOMER EXFOLIATING COMPOSITIONS

(75) Inventors: Fatemeh Mohammadi, Hauppauge, NY (US); Akshay Talati, East Meadow, NY (US); Anna Czarnota, Huntington, NY (US)

(73) Assignee: E-L Management Corp., New York, NY (US)

( * ) Notice: Subject to any disclaimer, the term of this patent is extended or adjusted under 35 U.S.C. 154(b) by 408 days.

(21) Appl. No.: 11/112,400

(22) Filed: Apr. 23, 2005

(65) Prior Publication Data

US 2006/0239949 A1    Oct. 26, 2006

(51) Int. Cl.
*A61K 8/02* (2006.01)
*A61K 8/00* (2006.01)

(52) U.S. Cl. .......................... 424/401; 424/69

(58) Field of Classification Search .............. 424/401
See application file for complete search history.

(56) References Cited

U.S. PATENT DOCUMENTS

| | | | |
|---|---|---|---|
| 5,837,793 | A | 11/1998 | Harashima et al. |
| 5,871,761 | A | 2/1999 | Kuwata et al. |
| 5,928,660 | A | 7/1999 | Kobayashi et al. |
| 6,238,656 | B1 | 5/2001 | Morita et al. |
| 2004/0126349 | A1 | 7/2004 | Anderson et al. |
| 2005/0036971 | A1 | 2/2005 | Kohlhase et al. |

FOREIGN PATENT DOCUMENTS

| | | |
|---|---|---|
| EP | 0295886 | 12/1988 |
| EP | 0 958 804 A2 | 11/1999 |
| JP | 11-335228 | 12/1999 |
| WO | WO 02/092047 | * 11/2002 |

OTHER PUBLICATIONS

Dow Corning 9509 Siliconeelastomer Suspension Product Information; Ref No. 27-1001-01; Aug. 17, 2001; taken from http://www.dowcorning.com/DataFiles/090007b580080e49.pdf.
Fresh, Energizing Lotion with Reduced Shine; Dow Corning formulation 00035; Jun. 14, 2001; taken from http://www.dowcorning.com/content/publishedlit/FORMUL_00035.pdf.
Matte Last Hydrogel: Mattifying; Dow Corning formulation 00231; taken from http://www.dowcorning.com/content/publishedlit/00231.pdf.
Shaving Jelly Clear Gel; Dow Corning formulation 00458; Jul. 8, 2003; taken from http://www.dowcorning.com/content/publishedlit/MENS_GROOMING_SOLUTIONS.pdf?DCAPP=WCMtechArticle.
Firming and Moisturing Body Fluid; National Starch formualtion 12002-63; Mar. 19, 2003; taken from http://www.personalcarepolymers.com/Doc/EN/FORMULATION/1200263.pdf.

* cited by examiner

*Primary Examiner*—Sreeni Padmanabhan
*Assistant Examiner*—Renee Claytor
(74) *Attorney, Agent, or Firm*—Peter Giancana

(57) ABSTRACT

Compositions of the present invention comprise from about 40-99% of an aqueous suspension of silicone elastomer powder in a cosmetically acceptable vehicle. The compositions are useful as skin exfoliants when mechanical agitation is supplied, for example by rubbing with a hand. After exfoliation, little or no film or residue remains on the skin and washing the treated area is optional. The cosmetically acceptable vehicle may comprise a wide range of beneficial ingredients, cosmetic or dermatological actives and additives. The present invention also encompasses a method of exfoliating skin in need of such treatment.

20 Claims, 1 Drawing Sheet

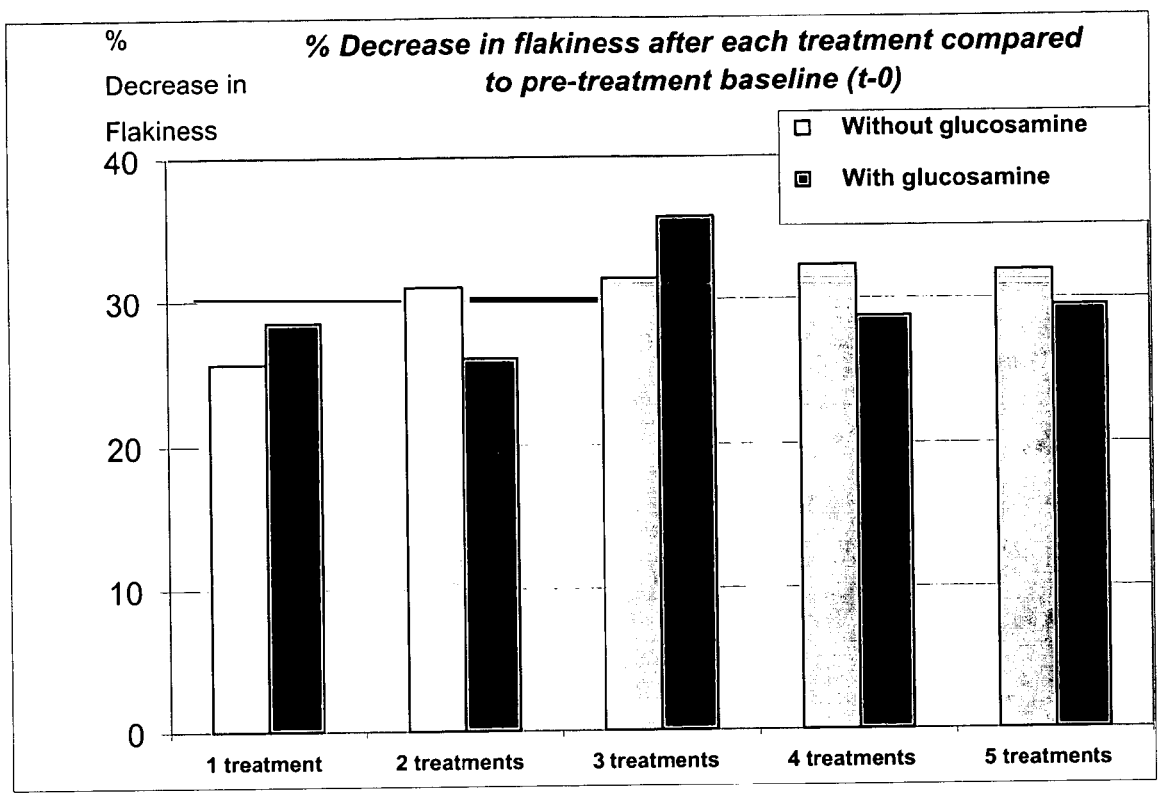

SILICONE ELASTOMER EXFOLIATING COMPOSITIONS

BACKGROUND

In the cosmetics and personal care industries, the use of silicone-based ingredients is well known. Generally, silicones have several very useful characteristics including high resistance to extreme temperatures, light stability, resistance to moisture and chemical exposure. Common applications for silicone products include their use as adhesives, surfactants and anti-foaming agents, while in cosmetics and personal care, silicones play a number of well defined roles that include smoothing, lubricating, moisturizing and conditioning.

One critical point is that silicone ingredients are used for their substantivity. Substantivity is the ability of a cosmetic ingredient to remain intact on the skin or hair even after the skin or hair has been rinsed with water. The advantage of good substantivity is that a conditioning agent can remain on the skin or hair for a considerable period of time to impart a benefit to the skin or hair. By considerable period of time, it is meant that the silicone ingredient is intended to remain intact on the skin or hair for at least several minutes or hours and is not easily removed, except with the aid of specific types of cleansers. In practice, cosmetic ingredients with good substantivity can remain on the skin or hair for hours or days and this is often intended. One drawback of ingredients with good substantivity is that they tend to build-up on the skin or hair with repeated applications over time. In time, this build-up itself becomes detrimental to the skin. In a novel way, the present invention utilizes silicone materials known for their good substantivity, while avoiding the problems of build up.

Some agents that exhibit good substantivity do so because of strong electrostatic attraction between the treated surface and the ingredient. Generally, silicones do not belong to this class. Silicones belong to a class of cosmetic ingredients that exhibit good substantivity because they are insoluble in water, and thus, once deposited on the skin or hair, are not easily washed away. Silicone products may be fluid, resinous or elastomeric, the exact form depending on the length of the polymer backbone and the degree of cross-linking. Because most silicones are not water soluble, significant research and development focuses on methods of incorporating silicone materials into aqueous delivery systems. In other words, the very property that gives silicones their excellent substantivity also complicates the formulation of silicones into stable, efficacious aqueous systems. For example, in cosmetics and personal care, where the product vehicle is frequently water based, it is often necessary to emulsify silicone oils and elastomers into an aqueous external phase using surfactants. This introduces additional complexity to the formula and full scale production, the costs of production are increased and additional limitations are placed on the formula because of the need to make an emulsion. For example, emulsifiers and surfactants are known to be skin irritants and so this needs to be taken into account. The present invention provides a stable, efficacious silicone elastomer formulation that is aqueous based, but may not require the addition of emulsifiers.

In the cosmetics industry, silicone elastomers may be considered as dry emollients. Emollients are agents that impart smoothness and lubricity to the skin or hair. In topical ointments, silicone elastomers impart sleekness and a silky and powdery feel to skin or hair. In make-up compositions they may also be used to modify shine or mattify the appearance of the skin and to impart long lasting waterproofing properties. Examples of known crosslinked silicone elastomers that are used for these purposes include the dimethicone-cyclomethicone and dimethicone-divinyldimethicone crosspolymers from Dow Corning; the organopolysiloxanes from Grant Industries known under the name Gransil; General Electric's dimethicone-vinyldimethicone crosspolymers and others. Although the elastomer is in powder form, once applied to the skin, as in prior art formulations, it still exhibits good substantivity and may not easily rinse off the skin. Compositions of the present invention are particularly concerned with solid silicone elastomers in powder form. However, the compositions herein described may be easily removed from the skin within seconds or minutes of their application without the aid of specific cleansers or removal agents or even a ready supply of water.

As mentioned, silicone elastomers may be incorporated into water based systems by emulsion techniques, however, it is also known to form suspensions of powdered silicone elastomers which may then be added to an aqueous base. Suspension of silicone elastomers will be preferred over emulsification when the silicone elastomer is non-hydrophilic, in nature and therefore, non-emulsifying. Suspending agents are generally used for this purpose. Silicone elastomer suspensions are also to be preferred over emulsion systems when it is desired to avoid the harsh, irritating side-effects of surfactants and emulsifiers or when it is desirable to reduce as mush as possible, the amount of these irritants. Furthermore, suspensions of the type contemplated are generally simpler to manufacture than emulsions.

One commercially available suspension of this type is Dow Corning© 9509 Silicone Elastomer Suspension, which is a 63% by weight, nonionic suspension in water, of powdered dimethicone/vinyl dimethicone crosspolymer (and) C12-14 pareth-12. According to a DC9509 Product Information Sheet (ref no. 27-1001-01; Aug. 17, 2001), the contents of which are herein, incorporated by reference, the silicone elastomer particles are spherical and have an average diameter of 3 µm. The range of particle sizes in DC 9509 is about 0.1 µm-100 µm. The recommended use of this material is by direct addition to an aqueous phase, such that the pure silicone elastomer is present at a level of 3-6 wt. % of the final formulation. Given that the suspension is 63 wt. % of silicone elastomer, the suspension should comprise approximately 5-10 wt. % of the final formulation in order to meet the manufacturer's recommendation of 3-6 wt. % silicone elastomer. In the Product Information Sheet, three examples are mentioned: a hydrogel containing 10% DC 9509, a hydrogel containing 8% DC 9509 and a water-in-silicone emulsion having 6.5% DC 9509 in the aqueous phase. Further examples of formulations with DC 9509 can be found at the websites of Dow Corning and National Starch. These include: Dow formulation 00035 Fresh Energizing Lotion with Reduced Shine, containing 10 wt. % DC 9509; Dow Formulation 00231 Matte Last Hydrogel, containing 5 wt. % DC 9509; Dow Formulation 00458 Shaving Jelly, containing 2 wt. % DC 9509; and National Starch 12002-63 Firming And Moisturizing Body Fluid, containing 6 wt. % DC 9509. In line with Dow's instructions, none of these formulations uses more than 10% DC 9509. The present invention includes stable and efficacious compositions with substantially more than 10% DC 9509.

U.S. Pat. No. 5,871,761 (the contents of which are herein, incorporated by reference) discloses a method of preparing water-based cosmetics comprising the steps of:

(a) preparing an aqueous dispersion (suspension) of globular (spherical) particles of a cured silicone rubber having a specified average particle diameter (0.1 to 100 µm, preferably 1 to 10 µm), by a particular method disclosed therein, and (b) mixing a specified amount of the aqueous dispersion of silicone rubber particles with a base mixture that consists of the principal ingredients of a water-based toiletry composition.

The content of silicone rubber particles is specifically limited to 0.1-30 wt. % (preferably 1-10 wt. %) of the total amount of the non-volatile matters in the base mixture. The silicone content of the aqueous dispersions formed in step (a) are disclosed to be in the range of 1-70 wt. % of the aqueous dispersion. Therefore, step (a) encompasses Dow Corning 9509, discussed above, which is a 63% aqueous dispersion.

The upper limit of 30% in step (b) is explained at column 6, lines 29-32 of the '761 patent, which reads: "When the amount of the cured silicone rubber particles is too large, the inherent role to be played by the water-base[d] toiletry preparation may not be satisfactorily played or the stability of the water-base[d] toiletry preparation is decreased." In other words, the '761 patent gives specific reasons for not formulating a water-based toiletry with silicone elastomers above about 30 wt. % of the total amount of the non-volatile matters in the base mixture. These reasons relate to a loss of efficacy and stability of the overall composition.

In practice, the prior art discloses uses of silicone elastomer powder at much lower than 30% of the weight of the non-volatile portion of the base mixture. In the four examples of the '761 patent, elastomer weight is less than 3%. In the four examples mentioned above (three from Dow Corning and one from National Starch), the silicone elastomer contents are between 1 and 8 wt. % of the total amount of the non-volatile matters in the base mixture. Thus, in practice, the prior art, including the '761 patent, has stayed well below the maximum amount of silicone elastomer powder recommended in the '761 patent. The present invention includes stable and efficacious compositions with DC 9509 at levels that are substantially more than 30% of the total amount of the non-volatile matters in the base mixture.

US publication 2004/0126349 discloses a non-emulsion, water-based composition comprising a suspended silicone elastomer. The preferred suspended elastomer is disclosed as DC 9509, which should be added to the composition at no more than 10% of the weight of the total composition, which is also the recommendation of Dow Corning, as discussed above. The preferred concentration of the silicone elastomer suspension is 0.1-5 wt. % and the most preferred is 0.5-2.5 wt. % of the total weight of the composition. In the only example in the publication, the weight of the silicone elastomer suspension is 2% of the total composition weight. The weight of the silicone elastomer itself, is less than 2 wt. % of the total amount of the non-volatile matters in the base mixture. Again, this is well below the upper limit disclosed in the '761 patent, discussed above and even further below the levels of the present invention.

US publication 2005/0036971 discloses high lipid-content, pearlescent cosmetic preparations comprising: $C_{12}$-$C_{40}$ fatty acids, $C_{12}$-$C_{40}$ fatty alcohols, amphophilic polymers and/or siloxane elastomers, sodium hydroxide solution and optionally $C_{12}$-$C_{40}$ polyethoxylated fatty acid esters. Preferred silicone elastomers are in spherical powder form, in suspension or emulsion and DC 9509 is disclosed as being particularly advantageous. The weight of pure silicone elastomer is disclosed as being from 0.5-10 wt. % of the total composition, although the examples demonstrate no more than 0.5 wt. % silicone elastomer in any composition. Again, this is well below the upper limit disclosed in the '761 patent, discussed above and even further below the levels of the present invention.

At paragraph [0074], the '971 publication teaches the following: "In addition, they [silicone elastomers] have stabilizing effects on formulations with a high content of oil and low water contents of at most 5% by weight." This statement of the prior art certainly suggests that silicone elastomers fail to stabilize compositions that comprise more than 5% water. Bearing in mind that DC 9509 is about 37% water, any composition comprising at least about 14% of DC 9509 automatically contains more than 5% water. Thus, the '971 publication suggests that no benefit is obtained by formulating compositions with more than 14% DC 9509. The present invention advantageously comprises substantially more than 14% DC 9509 or any equivalents of 14% of DC 9509.

To the best of the applicant's knowledge, and as demonstrated by the foregoing discussion, efficacious and stable personal care compositions comprising an aqueous suspension of silicone elastomer particles, such that the weight of the silicone elastomer is greater than 30 wt. % of the total amount of the non-volatile matters in the base mixture, are unknown in the prior art. In fact, the examples disclosed in the prior art are all substantially below this level. The present invention goes against the teachings of the prior art to provide stable and efficacious compositions having silicone elastomers at greater than 30 wt. % of the total amount of the non-volatile matters in the base mixture. Furthermore, the present invention includes compositions comprising substantially more than 5% water.

Cosmetic or dermatologic exfoliation is the process of removing dead or degraded layers of skin cells from the top most surface of the skin in order to expose healthier cells below. Cosmetic exfoliation has a number of known and generally accepted benefits which include: providing a healthier, more attractive appearance to the skin; providing a "glow" to the skin; opening or unblocking the pores of the skin to facilitate the receiving of topically applied nutrients or other treatment benefits; encouraging increased blood flow in the skin; encouraging collagen formation in the skin leading to thicker, firmer, healthier skin. Among other things, exfoliation has been used to treat acne, irregular pigmentation, signs of ageing and scarring. For these and other reasons, exfoliation is widely recognized as one of the most important skin treatments for persons interested in improving the health and appearance of their skin. Techniques include mechanical abrasives, like scrubs, peels, and dermabrasion; chemical exfoliants in the form of peels, masques and other topical ointments; and laser treatment. In the first instance, the present invention is concerned with mechanical abrasion for the benefits that such impart to the skin. However, the incorporation of chemical exfoliants or use in conjunction with laser treatment is not outside the scope of this invention.

One drawback of some exfoliation techniques, particularly conventional peels and masques, is that there is a substantial drying time that the user must wait before the peel or masque can be removed. Frequently, leaving a thick layer of ointment on an extended portion of the skin, especially the face, is physically uncomfortable and socially inconvenient, as some people receiving these treatments prefer not to be seen during the course of a treatment. Compositions of the present invention are applied in the manner of creams, lotions and ointments, but there is a substantially reduced drying time compared to the prior art, and the exfoliation may be completed in much less time than other products, thus alleviating the physical and social discomfort associated with exfoliation treatment.

Another drawback of some exfoliation products is that they must be removed from the skin by rinsing with water or some other cleanser. Failure to do so leaves a residue on the skin which generally, compromises the appearance of the skin, is uncomfortable for the user and may cause irritation to the skin of the user. For this reason, and because some people prefer not to be seen receiving an exfoliation treatment, mechanical exfoliation with a cosmetic product is generally done at home or in a salon where a ready supply of water and privacy are available. In contrast, exfoliants of the present invention may be used to impart a benefit to the skin and then be removed from the skin with little or no water for rinsing. The treatment may be completed quickly and far more inconspicuously than conventional exfoliation treatments. Therefore, a user need not feel limited to the home or salon for treatment.

European Patent 0295886 discloses facial cleansers comprising a spherical silicone elastomer powder. According to the description, ". . . the organopolysiloxane elastomer used in the present invention provides the facial cleanser of the present invention with a smooth application sensation and does not irritate the skin." Moreover, the specification says, "Prior facial cleansers which contain non-silicone powders have an unsatisfactory silicone-removal action because these powders lack any affinity for silicones. The organopolysiloxane elastomer powder has affinity for the silicone starting materials compounded in cosmetics and thus can remove silicones adhering on the skin." Thus, in these compositions, the silicone elastomer is used primarily for its chemical affinity to other silicones, to lift those silicones from the skin. It has the simultaneous benefit, according to the authors, of going on smoothly and not causing irritation to the skin. It is clear from other parts of this disclosure that when the authors say "irritation" they mean mechanical irritation that is typical of the non-spherical, sharp, hard cleansing agents of the prior art. Thus, this reference suggests that the spherical nature of the silicone elastomer and its relative softness are useful for reducing mechanical abrasion. Put another way, EP 0295886 suggests the use of spherical silicone elastomer powders to reduce the action of exfoliation. Indeed, there is no mention in this reference of any exfoliation type activity or benefit. Therefore, the use of silicone elastomer powder in EP 0295886 is unlike the present invention, which uses silicone elastomer powder in a composition for mechanical exfoliation.

The '866 patent further discloses the use of silicone elastomer powder up to 30% of the composition, when the composition is a cream or emulsion (up to 50% when the composition is a solid or paste). Here again, the prior seems united on this point, placing an upper limit on the content of the silicone elastomer powder at around 30% of the non-solid composition. And, like the previous references, the examples in the '866 reference disclose amounts of silicone elastomer powder well below 30%, in this case, no more than 5% of silicone elastomer powder is present in any actual composition.

Furthermore, the '866 patent is an example of the fact that the use of soft, spherical particles in a composition may be expected to reduce the mechanical exfoliation action of the composition. Indeed, silicone elastomers and other silicone products are noted for the emolliency, lubricity, sleekness and powdery fell that they impart to compositions. All of these things are contrary to the type of mechanical abrasion required in exfoliating products. Nevertheless the present invention uses spherical silicone elastomer powder in a novel way to create a new type of exfoliating product.

A final observation of the prior art should be made, here. Based on the actual examples disclosed in the prior art, the totality of the prior art suggests that the instability and loss of efficacy associated with silicone elastomer particles, as discussed above, begin to appear somewhere below 30%, especially if more than 5% water is present in the composition. Therefore, the 30% upper limit from U.S. Pat. No. 5,871,761 is more accurately understood as a point of no return, as it were, rather than merely the onset of stability and efficacy problems.

OBJECTS OF THE INVENTION

Objects of the present invention include:

Providing an exfoliation composition that delivers a pleasing sensorial experience and does not use harsh abrasives to exfoliate.

Providing an exfoliation regimen that is fast and convenient.

Providing an exfoliation regimen that may conveniently be done anywhere, no water being required.

Providing stable and efficacious aqueous-based silicone elastomer compositions that may be suspensions or emulsions.

Providing stable and efficacious compositions comprising silicone elastomer powders at concentrations substantially higher than the prior art would allow.

Providing an exfoliation composition that leaves substantially no residue on the skin even though the skin is not rinsed after treatment.

These and other objects and benefits are realized in compositions of the present invention herein described.

SUMMARY OF THE INVENTION

Exfoliating compositions of the present invention comprise from 30-99% of an aqueous suspension of silicone elastomer powder in a cosmetically acceptable vehicle. The cosmetically acceptable vehicle may be substantially aqueous or may have little or no water. The cosmetically acceptable vehicle may comprise a wide range of beneficial ingredients, cosmetic or dermatological actives and additives. Compositions of the present invention are useful as skin exfoliants when mechanical agitation is supplied, for example by rubbing with a hand. After exfoliation, little or no film or residue remains on the skin and washing the treated area is optional. The present invention also encompasses a method of exfoliation comprising applying to the skin, in need of such treatment, an exfoliating effective amount of an aqueous suspension of silicone elastomer powder in a cosmetically acceptable vehicle.

DESCRIPTION OF THE LONE FIGURE

The FIGURE compares results of exfoliation treatments utilizing compositions according to the present invention and particularly shows that compositions of the present invention are capable of completely exfoliating the skin.

DETAILED DESCRIPTION

Throughout this specification, the terms "comprise," "comprises," "comprising" and the like shall consistently mean that a collection of objects is not limited to those objects specifically recited. Furthermore, regarding compositions according to the present invention, all recitations of percent levels are to be understood as being "about" that level, unless otherwise noted.

It has been advantageously discovered that compositions comprising 40-99% of an aqueous suspension of silicone elastomer powder are stable and efficacious as exfoliation products. Aqueous suspensions of silicone elastomer powder that are useful in the present invention include, but are not limited to, those in which the particle size distribution ranges from about 0.1 μm-100 μm, preferably from 1-10 μm. Silicone elastomer suspensions having a concentration of silicone elastomer powder between 30-70% are useful for the present invention. One useful aqueous suspensions of silicone elastomer powder is DC 9509 from Dow Corning. DC 9509 may advantageously be used in the present invention at levels of 40 to 99%, preferably 50-90%, and most preferably 60-80%, by weight of the total composition. Since DC 9509 is a 63% solution of silicone elastomer, compositions of the present invention may advantageously comprise about 25-63% silicone elastomer powder, by weight, preferably 30-57%, and most preferably 37-50%. Any suspension of silicone elastomer powder meeting this concentration is within the scope of this invention and, at least in this sense, may be considered a functional equivalent of the Dow Corning 9509.

The aqueous suspension of silicone elastomer powder used in accordance with the present invention is combined with a cosmetically acceptable carrier and applied in forms that are normally used on the skin. The term "cosmetically acceptable carrier" refers to a vehicle that delivers the active components to the intended target and which will not cause harm to humans or other recipient organisms. As used herein, "cosmetic" will be understood to encompass both human and animal cosmetics with which the active component is compatible, e.g., a gel, a cream, a lotion, an ointment, a mousse, a spray, a solid stick, a powder, a suspension, a dispersion, and the like. Techniques for formulation of various types of vehicles are well known to those skilled in the art, and can be found, for example, in Chemistry and Technology of the Cosmetics and Toiletries Industry, Williams and Schmitt, eds., Blackie Academic and Professional, Second Edition, 1996, and Remington's Pharmaceutical Sciences, 18th Edition, 1990, the contents of which are incorporated herein by reference. The formulations employed can also include other cosmetic or pharmaceutical ingredients, e.g., moisturizers, humectants, anti-inflammatories, antioxidants, and the like.

The manner of using compositions according to the present invention is as follows. A sufficient amount of a composition according to the present invention is applied to an area of skin in need of exfoliation treatment. The composition may generally be applied by using a hand to perform a spreading action over the skin. If the amount applied to the area seems insufficient, additional spreading actions may be performed on top of the composition already on the skin. After the area to be treated has been satisfactorily covered by a spreading action, the user may immediately commence a rubbing action of the composition on the skin or the user may wait several seconds or minutes before beginning a rubbing action. While the most convenience may be achieved by compositions wherein the rubbing action commences immediately, the present invention allows for intentional delay. A delay may be appropriate when time is needed for the composition to perform some other function before mechanical exfoliation. For example, time may be needed to prepare the skin for mechanical exfoliation. Perhaps a cleanser or chemical exfoliant will be allowed to work first. As another example, the composition may contain features of a purely sensorial nature, to impart a luxurious feeling to the user. In either case, the rubbing action is generally more firm than the spreading action, but not difficult to perform. Within seconds or minutes of commencing the rubbing action (depending on the firmness of the rubbing), the composition on the skin will pill into visible flakes. The rubbing action, unlike the spreading action, is characterized by the pilling of the composition. The spreading action may cause some incidental amount of pilling, but this is unlike the significantly greater amount of pilling caused by the firmer rubbing action. As the rubbing action progresses, a sufficient quantity of flakes appears on the skin to initiate some exfoliation. During this time, flaking and exfoliation may occur simultaneously. However, within several seconds or minutes of commencing the rubbing action, the formation of flakes will be complete. All of the composition that is going to flake, has flaked and, at this point, continued or extended rubbing action causes the maximum amount of exfoliation. As a result of the extended rubbing, dead skin, skin metabolites and skin surface adherents transfer to the flakes. This would not happen with the spreading action alone, nor without the extended rubbing action. During the extended rubbing action, the rubbing must be sufficiently energetic to cause the exfoliation described, but this is not difficult. During the extended rubbing action, the flaked composition may be allowed to fall off the skin, taking with it, significant amounts of dead skin, skin metabolites and other skin surface adherents. Alternatively or additionally, the flakes may be removed from the exfoliated skin by other means, such as rinsing with water or patting with a towel. Advantageously, the flakes, combined with the extended rubbing action, provide an effective mechanical exfoliation of the skin.

For purposes of forming a mental image, the appearance of the flakes themselves may me thought of as similar to those produced by using a rubber pencil eraser. Although varying in size, the flakes are easily visible to the unaided eye and may be, for example from 1-5 mm in length. They are, therefore, generally larger than the silicone elastomer particles in the DC 9509. It is important to realize that these larger flakes are what is providing the effective exfoliation and absent these flakes, effective mechanical exfoliation would not take place. The pure silicone particles themselves are not effective exfoliants. This is not surprising since the pure silicone powder is generally used for increasing lubricity and decreasing the type of friction needed for effective exfoliation. In contrast, the flakes are much larger than silicone spheres and they are irregularly shaped rather than spherical. One theory of the present invention's efficacy is that the size and irregular shape of the flakes cause them to have more contact with the skin than the spherical silicone particles in the base material. The degree of contact with the skin makes the flakes useful as mechanical exfoliants. At the same time, the flakes retain some of the softness of the silicone elastomer and so the flakes, while being effective for exfoliation, are not nearly as harsh as many mechanical exfoliant materials.

As discussed above, compositions of the present invention may advantageously comprise about 25-63% silicone elastomer powder, by weight, preferably 30-57%, and most preferably 37-50%. These levels of silicone elastomer powder define exfoliating effective amounts. By "exfoliating effective amount" it is meant that the amount of silicone elastomer power, when combined with rubbing, is sufficient to produce useful pilling. When less than this amount of silicone elastomer powder is used, the degree of pilling as a result of rubbing, if any, is not useful. By "useful pilling", it is meant that the amount of flaking as a result of rubbing is sufficient, in combination with extended rubbing, to cause an effective exfoliation treatment. By "effective exfoliation treatment" it is meant that skin flakiness is reduced by at least about 10% relative to a baseline, preferably at least about 20%. Decrease in skin flakiness may be measured by any standard method known to be used for this purpose, for example, using D-squame discs with image analysis.

The aqueous suspension of silicone elastomer powder used in accordance with the present invention is combined with a cosmetically acceptable carrier and applied in forms that are normally used on the skin. A wide range of cosmetically and pharmaceutically acceptable materials may be advantageously used to preserve or alter the physical properties of the composition in order to create for the user a unique and pleasurable sensorial experience. For example, without departing form the spirit of the invention, an effective amount of one or more of the following may be included: abrasives, absorbents, anti-caking agents, antifoaming agents, antifungal agents, antimicrobial agents, antioxidants, binders, biocides, buffers, bulking agents, colorants, corrosion inhibitors, deodorants, film formers, fragrance, humectants, opacifiers, oxidizers, pH adjusters, plasticizers, preservatives, propellants, reducing agents, slip modifiers, solvents, stabilizers, surfactants, viscosity controlling agents. In addition, a wide range of cosmetically and pharmaceutically acceptable materials and actives may be used to provide a benefit to the skin. These include an effective amount of one or more of the following: abrasives, absorbents, antiacne agents, anti-ageing agents, antifungal agents, anti-inflammatories, antimicrobial agents, antioxidants, antiperspirants, astringents, biocides, chemical exfoliants, cleansers, deodorants, depilating agents, epilating agents, external analgesics, humectants, make-up removers, skin bleaching agents, skin conditioning agents, skin protectants, sunscreens, tanning agents and UV absorbers. Just about any cosmetic, dermatologic or pharmaceutic agent suitable for topical use, is within the purview of this invention, the only requirement being that overall composition must function effectively as an exfoliant when used in the in the manner described above.

By way of example, dimethicone, trimethicone, cyclomethicone, straight chained hydrocarbons and their esters and polyols have proved useful to impart an elegant feel, texture or consistency to the composition. In general, any known prior art cosmetic formulation techniques may be useful with compositions of the present invention.

After an exfoliating treatment using a composition according to the present invention, the skin may not need to be rinsed with water. Preferably, after an exfoliating treatment using a composition according to the present invention, the skin does not need to be rinsed with water. Substantially all of the flaked composition will have been rubbed off. Substantially all of the composition may be flaked off when within several seconds, or at most five minutes, no silicone residue on the treated skin can be detected by the human eye, or in the feel of the skin. Preferably, substantially all of the composition can be removed within two minutes of applying a rubbing action, most preferably within one minute. If the flaked composition rubs off too fast, exfoliation may not be complete. If it rubs off too slowly, the practical, time saving and convenience benefits will be compromised. Because the treatment does not require a rinsing action to complete, the user is not restricted to venues having a supply of rinsing water. This is a significant advantage over prior art exfoliants. Also, because the treatment is completed relatively quickly, a user may feel free to perform such treatments in less than total privacy, because the likelihood of being seen is significantly reduced. For example, the present invention may be ideal for a quick refreshing, "pick-me up" at the office, in the middle of the day, just before meeting with an important client.

Even though the compositions may not remain on the skin for more than a minute or two, it should be remembered that exfoliating compositions according to the present invention are at least somewhat effective at opening up the pores of the skin and unclogging the pores of skin. Therefore, it is realistic to expect that cosmetically active agents incorporated into the composition, will have lasting beneficial effects even after the treatment is over, because at least some of those agents will find their way into the pores of the skin and remain in the skin. As such, compositions according to the present invention may be used a delivery vehicle for incorporating cosmetic and dermatologic materials into the pores of the skin.

Formulations of the present invention may be applied on an as-needed basis, to "resurface" skin that is temporarily afflicted with a patchy, flaky or irregular texture. In many cases, however, application of the formulation will be chronic, to remedy a long-term reduction in the natural exfoliation process. For example, if needed, exfoliation treatments with the present invention may be performed from about once per week to about 4 or 5 times daily, preferably from about 3 times a week to about 3 times daily, most preferably about once or twice per day. By "chronic" application, it is meant herein that the period of topical application may be over the lifetime of the user, preferably for a period of at least about one month, more preferably from about three months to about twenty years, more preferably from about six months to about ten years, more preferably still from about one year to about five years. Advantageously, compositions of the present invention are easier to use than prior art exfoliating compositions, therefore, a person in need of chronic application is more likely to remain committed to a long term treatment regimen.

Compositions of the present invention may be used alone or as part of a skin treatment regimen. For example, a post exfoliation toner may be used to supply the exfoliated skin with nutrition, a refreshing feeling, fragrance, color, optical enhancements, additional cleansing or any other cosmetic or dermatologic advantage. Freshly exfoliated skin may be particularly ready to receive and utilize skin treatment and beautifying products.

The following non-limiting examples may be useful for understanding the invention. Compositions in the examples are stable and effective as exfoliating compositions.

EXAMPLE 1

Clinical Study

The following is a description of a clinical study carried out for the purpose of evaluating the exfoliation effectiveness of compositions according to the present invention Summary of Clinical Study Two versions of an exfoliating composition followed by post peel toners were tested on two groups of women. These compositions are shown below, see "Test Products". For comparison, the group 2 composition contained 5% N-Acetyl D-Glucosamine, (a known chemical exfoliant) followed by a toner with 2% N-Acetyl D-Glucosamine. The group 1 composition and post peel toner contained no N-Acetyl D-Glucosamine, nor any other exfoliating agent.

Each composition was applied to a clean face and allowed to sit for 20 minutes, it was then peeled off in the rubbing manner described above. The treated area was then cleansed with cotton balls soaked in the toner.

Skin evaluation was carried out every day for 5 days before and fifteen minutes after treatment. Skin exfoliation was evaluated by measuring the amount of flakes removed from the skin surface using D-squame discs and analyzing them via the IA method.

Experimental Design

Subject selection—Twenty-six women, thirteen per group, successfully completed the study. The women were informed in detail as to the purpose and requirements of this study and were admitted if they met the following criteria. The test area was their entire face. The subjects refrained from using cosmetic products on their face for least 10 hours before the test. They reported to the testing facility with clean, washed skin. All volunteers gave their informed written consent before beginning the test.

Inclusion criteria—Volunteers met the following criteria:
1. Are 25-65 years of age.
2. Have normal to dry skin on their face.
3. Have good general health with no evidence of acute or chronic disease including dermatological or ophthalmic problems.

Exclusion criteria—Volunteers presented none of the following:
1. Have any kind of skin disease (infection, inflammation, sunburn, tumor) in the test area.
2. Have a history of hypersensitivity or allergy to cosmetic products.
3. Are pregnant or lactating women.

Test Procedures

At each visit the subjects showed up with a clean face washed at least 1 hour prior to testing. D-squame skin samples were taken according to the procedures described below. A composition was applied on their face for 20 minutes; it was then peeled off, cleansed with cotton balls soaked in a toner and reevaluated 15 minutes later. The group 1 toner, applied with cotton balls, provided no additional exfoliation. On the first day the subjects were given a tube of moisturizer to use once or twice a day, exclusively, in place of their regular moisturizer and, for the duration of the study, refrained from any other treatment. The subjects returned the next 4 days and the test procedures were repeated under the same conditions.

Skin exfoliation via D-Squame Discs Method and Image Analysis—Four D-squame discs were firmly and evenly pressed on the face (two on each side) with a hand held uniform pressure device and removed by gently pulling away from the skin. The D-squame discs were mounted on clear microscope slides and labeled according to panelist name and visit. Desquamation was evaluated from the D-squame discs via the image analyzer. This evaluation was carried out before and after treatment, every day for 5 days.

The OPTIMA image analyzer was used to evaluate skin flakiness. The D-squame samples containing the stratum corneocytes were placed under a camera on top of a light table and each image was imported into the image analyzer. The average Gray Value corresponding to the sample density was measured. The denser the sample the higher the Gray value difference.

| Test Products | | |
|---|---|---|
| Exfoliating composition | Group 1 | Group 2 |
| DC 9509 silicone elastomer | 79.545 | 79.545 |
| Methyl trimethicone | 16.882 | 12.590 |
| Silicone HL88 | 2.690 | 2.000 |
| Phenoxyethanol | 0.750 | 0.750 |
| ARISTOFLEX AVC* | 0.100 | 0.100 |
| L-arginine | 0.033 | 0.015 |
| N-acetyl-D-glucosamine | — | 5.000 |

*ammonium acrylodimethyltaurate/VP copolymer

Procedure
1. Into the main vessel add DC 9509 Silicone Elastomer.
2. Maintain temperature at 25 C.
3. Start Homogenizer and side wipe mixing.
4. Add N-Acetyl-D-Glucosamine and mix for 15 minutes and to ensure that the batch is uniform and all powder is completely dissolved. (for group 2 only)
5. Add L-Arginine. Mix for 5 minutes.
6. Slowly sprinkle in Aristoflex AVC. Adjust homogenizer speed to slightly higher. Continue homogenizer and side wipe mixing for 30 minutes. Ensure that batch is smooth and uniform without and gel lumps.
7. Add Phenoxyethanol and mix for 10 minutes.
8. Premix TMF-1.5 and Silicone HL 88 in a separate vessel using a propeller mixer. Mix for 10 minutes.
9. Slowly add the premixed blend of TM-1.5 and Silicone HL 88 to the main vessel. Continue homogenizer mixing and side wipe mixing. Adjust speed if necessary.
10. Once batch is uniform stop all mixing and transfer the bulk to appropriate containers.

| Post exfoliation toner | Group 1 | Group 2 |
|---|---|---|
| Deionized water | 90.170 | 88.170 |
| 1,3 Butylene glycol | 2.500 | 2.500 |
| Glycerine USP 99% (vegetable) | 2.000 | 2.000 |
| Sucrose, ultra pure | 2.000 | 2.000 |
| Activera 1:1 P* | 0.500 | 0.500 |
| Actiphyte of chamomile BG50NP | 0.500 | 0.500 |
| Actiphyte of cucumber BG50NP | 0.500 | 0.500 |
| Phenoxyethanol | 0.350 | 0.350 |
| Actiphyte of quince seed BG50NP | 0.300 | 0.300 |
| Green tea extract | 0.300 | 0.300 |
| Sodium citrate | 0.230 | 0.230 |
| Methyl paraben NF | 0.200 | 0.200 |
| Caffeine powder | 0.200 | 0.200 |
| Disodium EDTA | 0.200 | 0.200 |
| Citric acid - anhydr. USP-FCC (granu.) | 0.050 | 0.050 |
| N-acetyl-D-glucosamine | — | 2.000 |

*Aloe barbadensis leaf juice

Results and Discussion

Graph 1 in the figure summarizes the results of the study. The results show that both compositions significantly decreased skin flakiness after each treatment compared to pre-treatment baseline. The difference between results obtained with each composition is statistically insignificant. By adding glucosamine to the composition, no statistically significant increase in exfoliation was observed. This result strongly suggests that at least some compositions according to the present invention, without glucosamine (or any other exfoliant for that matter), may be able to perform complete exfoliation of the skin. Whether or not any additional benefit is obtained, by incorporating known exfoliants into compositions of the present invention may be determined by repeating this experiment. Exfoliation is the process of removing dead or degraded layers of skin cells from the top most surface of the skin in order to expose healthier cells below. The benefits of exfoliation have been discussed above. This clinical study demonstrates that compositions of the present invention are effective for the purposes and benefits of exfoliation.

It has been emphasized that the present invention may be applied and peeled off within one or two minutes. In this experiment, the dwell time on the skin was 20 minutes. The reason for this was to give the group 2 composition with chemical exfoliant, glucosamine, time to work. For consistency, the group 1 composition, without glucosamine, was left on the face for the same amount of time.

EXAMPLES 2-7

The following compositions according to the present invention are effective as exfoliating products. Generally, compositions of the following examples, and variations thereof, may range from medium viscosity lotions to a thick creams or gels. Amounts are weight percent.

| Example 2 | |
|---|---|
| DC 9509 Silicone Elastomer Suspension | 76.570 |
| Caprylyl Glycol/Phenoxyethanol/Hexylene Glycol | 0.750 |
| Polysorbate 20 | 0.200 |
| Hydrogenated Lecithin | 0.200 |
| Ammonium acrylodimethyltaurate/VP copolymer | 0.100 |
| Dimethicone | 22.000 |
| FD&C Red no. 4 (1% aq.) | 0.040 |
| FD&C Yellow no. 5 (1% aq.) | 0.040 |
| Fragrance | 0.100 |

| Example 3 | |
|---|---|
| DC 9509 Silicone Elastomer Suspension | 74.425 |
| Phenoxyethanol | 0.750 |
| Caffeine Powder | 0.200 |
| Sucrose | 0.500 |
| Yeast extract | 1.000 |
| Ammonium acrylodimethyltaurate/VP copolymer | 0.100 |
| Alcalinenes polysaccharides | 0.025 |
| Methyl trimethicone | 20.000 |
| Cyclopentasiloxane | 2.000 |
| Timiron Silk Blue 17241 | 0.040 |

| Example 4 | |
|---|---|
| DC 9509 Silicone Elastomer Suspension | 69.250 |
| Caprylyl Glycol/Phenoxyethanol/Hexylene Glycol | 0.750 |
| Ammonium acrylodimethyltaurate/VP copolymer | 0.100 |
| Dimethicone | 15.000 |
| Methyl trimethicone | 15.000 |

| Example 5 | |
|---|---|
| DC 9509 Silicone Elastomer Suspension | 68.000 |
| Denatured alcohol | 20.000 |
| Methyl trimethicone | 10.000 |
| Dimethicone | 2.000 |

| Example 6 | |
|---|---|
| DC 9509 Silicone Elastomer Suspension | 75.000 |
| Ethylhexyl isononanoate, Isododecane diethylene glycol diethylexanoate | 20.000 |
| Trimethylsilylamodimethicone/C11-15 pareth-7 C12-16 pareth-9/glycerin/trideth-12 | 5.000 |

EXAMPLE 7

The following cream demonstrates compositions according to the present invention may contain a variety of cosmetically acceptable ingredients that impart benefits to the skin or to the composition. At least some of those benefits may be enhanced by their presence on the skin during and immediately after an effective exfoliation treatment.

| DC 9509 Silicone Elastomer Suspension | 75.972 |
|---|---|
| Phenoxyethanol | 0.500 |
| BHT | 0.050 |
| 1,3 Butylene glycol | 3.000 |
| N-acetyl-d-glucosamine | 2.000 |
| Deionized water | 3.000 |
| Creatine | 0.010 |
| L-arginine | 0.015 |
| Disodium EDTA | 0.050 |
| Adenosine phosphate | 0.058 |
| Caffeine powder | 0.200 |
| ammonium acrylodimethyltaurate/VP copolymer | 0.200 |
| Methyl trimethicone | 3.000 |
| Dimethicone | 4.000 |
| Water/Chestnut extract | 0.100 |
| Polygonum cuspidatum root extract/declustered water/saccharomyces lysate extract | 0.010 |
| Yeast extract | 0.520 |
| Water/Butylene glycol/*Oryza sativa* (rice) bran extract | 0.010 |
| Water/Butylene glycol/laminaria saccharina extract | 0.500 |
| Titanium dioxide | 0.500 |
| Water/salicylic acid/sodium hydroxide butylene glycol/DI-C12-12 alkyl dimonium chloride | 4.500 |
| Allyl methylacrylates crosspolymer/salicylic acid | 0.200 |
| Ammonium acrylodimethyltaurate/VP copolymer | 1.400 |
| Color | 0.205 |

EXAMPLE 8

The following composition was taken from the Dow Corning web site and identified as Dow Corning formulation 00231, Mattifying Hydrogel (Oct. 17, 2003; http://www-.dowcorning .com/content/publishedlit/00231 .pdf).

| | | Wt. % |
|---|---|---|
| Phase A | | |
| 1. | Acrylates/C10-30 Alkyl Acrylate Crosspolymer | 0.200 |
| 2. | Distilled water | 75.850 |
| 3. | Propylene glycol | 5.000 |
| 4. | DMDM hydantoin | 0.300 |
| 5. | Dow Corning ® 9509 | 5.000 |
| Phase B | | |
| 6. | Cyclomethicone | 9.000 |
| 7. | *Sesamum indicum* (sesam) seed extract/*Argania spinosa* kernel oil/*serenoa serrulata* Fruit Extract | 4.000 |
| 8. | Perfume | 0.200 |
| Phase C | | |
| 9. | Sodium hydroxide | 0.045 |
| 10. | Deionised water | 0.405 |

Procedure

1. Agitate water enough to create a vortex. A pitched angle, three blade mixer works well. Slowly sift the Carbopol powder over the vortex. A sieve or mesh screen is recommended for this. Continue to mix and speed up the mixer if necessary to ~1200 rpm until particles swell and become invisible. Reduce speed to ~300 rpm to prevent foaming and continue mixing to allow the Carbopol to hydrate.

2. Add ingredient 3 and mix.
3. Add ingredient 4 with mixing.
4. Add ingredient 5 with mixing.
5. Premix ingredients of phase B (until homogenous)
6. Add phase B to Phase A, while properly mixing.
7. Premix phase C. Make sure to add Sodium Hydroxide to water slowly. Mix gently until dissolved.
8. Add phase C to the batch and continue to mix. The batch should become more viscous. pH should rise to 6.0-6.2.

This composition, representing a use of DC 9509 at levels typical of the prior art, did not pill when used in a manner described herein and therefore, is ineffective as an exfoliating composition according the present invention.

EXAMPLE 9

The following compositions were made to gain a better understanding of the pilling phenomenon. The results indicate that when a composition of 30% DC 9509 is used in the manner of the present invention, no useful pilling was observed. However, by 40% and beyond, useful pilling was observed.

| DC 9059 | Water | Comment |
|---------|-------|---------|
| 30% | 70% | no useful pilling |
| 40% | 60% | useful pilling |
| 50% | 50% | more pilling |

Given that the prior art teaches the use of DC 9509 at concentrations below 30%, while the practical examples of the prior art are consistently much lower than 30%, compositions comprising 40% or more go against the teaching of the prior art. Furthermore, to the extent that "instability" (at least what the prior art characterizes as instability) may be observed with compositions approaching 30% silicone elastomer suspension, it is contrary to common sense to think that continuing on to 40% or more, silicone elastomer suspension, is going to yield a useful product. But this is an unexpected benefit realized in the present invention. Furthermore, that the useful product turns out to be an exfoliating composition is particularly unexpected, in light of the prior art which nowhere contemplates silicone elastomer suspensions for use as exfoliating agents. In fact, relatively soft, spherical silicone elastomer particles are generally used for emolliency and lubricity, antithetical to mechanical abrasion.

What is claimed is:

1. An exfoliating composition comprising an exfoliating-effective amount of silicone elastomer powder, wherein the amount of silicone elastomer powder by weight of the total composition is between 37 and 50%.

2. The composition of claim 1 wherein the silicone elastomer powder is added to the composition in the form of an aqueous suspension.

3. The composition of claim 2 wherein the silicone elastomer suspension is Dow Corning© 9509 Silicone Elastomer Suspension or its functional equivalent.

4. The composition according to claim 1 wherein the particle size of the silicone elastomer powder is between 0.1 µm-100 µm.

5. The composition according to claim 4 wherein the particle size of the silicone elastomer powder is between 1 µm-10 µm.

6. The composition according to claim 1 comprising a cosmetically acceptable carrier.

7. The composition of claim 6 further comprising an effective amount of one or more cosmetically acceptable materials used to preserve or alter the physical properties of the composition, selected from the following: abrasives, absorbents, anti-caking agents, antifoaming agents, antifungal agents, antimicrobial agents, antioxidants, binders, biocides, buffers, bulking agents, colorants, corrosion inhibitors, deodorants, film formers, fragrance, humectants, opacifiers, oxidizers, pH adjusters, plasticizers, preservatives, propellants, reducing agents, slip modifiers, solvents, stabilizers, surfactants, viscosity controlling agents.

8. The composition of claim 6 further comprising an effective amount of one or more cosmetically acceptable materials or actives used to provide a benefit to the skin, selected from the following: abrasives, absorbents, antiacne agents, anti-ageing agents, antifungal agents, anti-inflammatories, antimicrobial agents, antioxidants, antiperspirants, astringents, biocides, chemical exfoliants, cleansers, deodorants, depilating agents, epilating agents, exfoliants, external analgesics, humectants, make-up removers, skin bleaching agents, skin conditioning agents, skin protectants, sunscreens, tanning agents and UV absorbers.

9. A method of exfoliating skin, comprising:
spreading on the skin a composition comprising an exfoliating effective amount of an aqueous suspension of silicone elastomer powder wherein the amount of silicone elastomer powder by weight of the total composition is between 37 and 50%;
rubbing the composition on the skin such that flakes appear on the skin;
rubbing the flakes on the skin to cause exfoliation of the skin.

10. The method of claim 9 wherein the step of spreading may be repeated before the step of rubbing the composition is commenced.

11. The method of claim 9 wherein rubbing the composition commences immediately after the spreading or wherein there is a delay between spreading and rubbing the composition.

12. The method of claim 9 further comprising the step of cleaning the exfoliated skin.

13. The method of claim 12 wherein the skin is cleaned by rubbing the flakes off the exfoliated skin.

14. The method of claim 13 which is performed in less than two minutes.

15. The method of claim 9 wherein the flakes are visible to the unaided eye.

16. The method of claim 15 wherein the flakes are between 1-5 mm in length.

17. The method of claim 9 wherein the flakes are irregularly shaped.

18. The method of claim 9 wherein the composition comprises a cosmetically acceptable carrier.

19. The method of claim 18 wherein the composition further comprises an effective amount of one or more cosmetically acceptable materials used to preserve or alter the physical properties of the composition, selected from the following: abrasives, absorbents, anti-caking agents, antifoaming agents, antifungal agents, antimicrobial agents, antioxidants, binders, biocides, buffers, bulking agents, colorants, corrosion inhibitors, deodorants, film formers, fragrance, humectants, opacifiers, oxidizers, pH adjusters, plasticizers, preservatives, propellants, reducing agents, slip modifiers, solvents, stabilizers, surfactants, viscosity controlling agents.

20. The method of claim 18 wherein the composition further comprises an effective amount of one or more cosmetically acceptable materials used to provide a benefit to the skin, selected from the following: abrasives, absorbents, anti-acne agents, anti-ageing agents, antifungal agents, anti-inflammatories, antimicrobial agents, antioxidants, antiperspirants, astringents, biocides, chemical exfoliants, cleansers, deodorants, depilating agents, epilating agents, external analgesics, humectants, make-up removers, skin bleaching agents, skin conditioning agents, skin protectants, sunscreens, tanning agents and UV absorbers.

* * * * *